United States Patent [19]

Yamamoto et al.

[11] 4,422,976

[45] Dec. 27, 1983

[54] CONTINUOUS PREPARATION OF ORGANIC ISOCYANATES

[75] Inventors: Ryuichi Yamamoto; Akinobu Takagi; Masafumi Kataita; Kenji Obata; Shigeki Mori, all of Ohmuta, Japan

[73] Assignee: Mitsui Toatsu Chemicals, Incorporated, Japan

[21] Appl. No.: 364,894

[22] Filed: Apr. 2, 1982

[30] Foreign Application Priority Data

Apr. 7, 1981 [JP] Japan .................................. 56-51216
Nov. 18, 1981 [JP] Japan ................................. 56-183734

[51] Int. Cl.$^3$ ........................................... C07C 118/02
[52] U.S. Cl. ............................................. 260/453 PH
[58] Field of Search ................................. 260/453 PH

[56] References Cited

U.S. PATENT DOCUMENTS

| 2,822,373 | 2/1958 | Beck .............................. | 260/453 PH |
| 3,184,494 | 5/1965 | Maeda et al. ................. | 260/453 PH |
| 3,234,253 | 2/1966 | Cooper .......................... | 260/453 PH |
| 3,544,611 | 12/1970 | Michelet et al. ............. | 260/453 PH |

*Primary Examiner*—Dolph H. Torrence
*Attorney, Agent, or Firm*—McGlew and Tuttle

[57] ABSTRACT

A two-stage continuous preparation process for organic isocyanates uses a primary amine which is reacted with stoichiometrically excess phosgene at a gauge pressure of 10 Kg/cm$^2$ or lower and a temperature of 60°–100° C. in an inert organic solvent. Then, the resultant reaction mixture is maintained at a gauge pressure of 10 Kg/cm$^2$ or lower and a temperature of 120°–160° C. until the reaction is completed.

12 Claims, 4 Drawing Figures

CONTINUOUS PREPARATION OF ORGANIC ISOCYANATES

BACKGROUND OF THE INVENTION (a) Field of the Invention

This invention relates to an improved preparation process for organic isocyanates from their corresponding organic primary amines (hereinafter simply called "amines") and phosgene. More particularly, it relates to a continuous preparation process for organic isocyanates in two stages, both under pressure, from their corresponding amines and phosgene.

(b) Description of the Prior Art

Organic isocyanates, especially, aromatic polyisocyanates such as tolylenediisocyanate (hereinafter called "TDI") and diphenylmethane diisocyanate (hereinafter called "MDI") have been produced recently in large amounts by phosgenating their corresponding primary amines in an inert organic solvent such as o-dichlorobenzene. Great profitability may be derived from even a small amount of economical improvement, if such an improvement is incorporated in the preparation of a product which is produced in large amounts as mentioned above. Accordingly, such an improvement has an extremely important significance from an industrial viewpoint.

A number of processes have been proposed to obtain such isocyanates through reactions between their corresponding amines or salts thereof and phosgene.

Many of such prior art processes are however accompanied by such drawbacks that they cannot provide any high yield over 90% or, even if such a high yield is available, they require maintaining the concentrations of their reactants at a very low level or they take an extremely long period of reaction time. Thus, they have been found unsuitable for application on an industrial scale.

Many of such prior art processes make use of a reaction method in which, in the case of TDI for instance, liquid phosgene or an inert solvent solution of phosgene is reacted at a low temperature below 30′–40° C. with an inert solvent solution of its corresponding amine so as to convert a part of amino groups into carbamyl chloride or amine hydrochloride and the resultant reaction mixture is then heated to 100°–180° C. to convert both carbamyl chloride and unreacted amine hydrochloride, the latter having been byproduced in the course of the reaction, into the isocyanate by feeding phosgene into the reaction mixture.

According to the above reaction method, the reaction may be carried out in various reaction vessels, including tank-shaped reaction vessels, tower-shaped reaction vessels and recirculating lines. It has also been proposed to conduct phosgenation by using each amine and phosgene in a special molar ratio or to carry out phosgenation in the presence of a special catalyst or under high pressures.

In Equation (1), the reaction between the amine and phosgene proceeds very fast even at low temperatures. In the course of the reaction, an amine hydrochloride is by-produced. The formation of carbamyl chloride through the reaction between the thus-formed amine chloride and phosgene—Equation (2)—is relatively low and can barely take place at low temperatures. Accordingly, it is commonly carried out to heat, while feeding phosgene, the reaction mixture to 100°–180° C. so as to convert unreacted amine hydrochloride into the isocyanate and, at the same time, to decompose the carbamyl chloride into the isocyanate in accordance with Equation (3).

Here, carbamyl chloride starts to decompose rather readily by heating the same and is decomposed almost completely at a temperature of about 120° C. or higher. However, the reaction velocity between unreacted amine hydrochloride and phosgene is relatively slow. If the reaction temperature is raised to accelerate the latter reaction, the isocyanate resulting from the decomposition of carbamyl chloride tends to react with the amine hydrochloride, leading to the formation of an undesirable urea compound. The urea compound in turn reacts with phosgene or undergoes polycondensation with the isocyanate, resulting in the occurrence of varied complex side reactions and the formation of tar-like substances as by-products. Thus, the use of a high reaction temperature has been considered as a major cause for a lowered yield.

A variety of improved processes have also been proposed to conduct the phosgenation of amine hydrochlorides at as low a temperature as possible and to obtain isocyanates with a good yield. For example, Japanese Patent Publication No. 14664/1964 (U.S. Pat. No. 3,184,494) discloses a method in which a reaction of Equation (1) is carried out at a temperature near room temperature in a first step, the reaction product of the first step is then completely converted into carbamyl chloride in a second step in accordance with Equation (2) by effecting the conversion at 60°–80° C. for 4 to 8 hours, and the carbamyl chloride is decomposed in a third step in accordance with Equation (3) into isocyanate so as to obtain the isocyanate with a good yield. This method is however not satisfactory from an industrial viewpoint for producing TDI or MDI in large amounts because it requires a very long reaction time and the concentrations of reactants cannot be raised too much and it thus requires a reaction vessel of a large capacity.

It may be considered to make the first step by continuously conducting the reaction at 60°–80° C. with a view toward obviating the above-mentioned drawbacks. Unless the reactants are well mixed at the initial reaction stage, by-products will be increased and carbamyl chloride will deposit on the walls of the reaction vessel as disclosed in Japanese Patent Laid-open No. 56635/1978 (U.S. Pat. No. 4,096,165). Moreover, an additional reaction vessel is required to achieve sufficient residence time so that the reactants can be completely converted into carbamyl chloride.

As prior art publications disclosing a process enabling mass production in a reaction vessel of a relatively small capacity may be mentioned for example Japanese Patent Publication Nos. 10774/1960, 17381/1965 and 6126/1976 (U.S. Pat. Nos. 2,822,373; 3,234,253; and 3,544,611 respectively). According to Japanese Patent Publication No. 10774/1960, an isocyanate-containing solution is recirculated along a closed loop at a carbamyl chloride-decomposing temperature or higher and an amine is charged into the thus-recirculating isocyanate-containing solution so as to cause the amine to react with the isocyanate immediately. Then, by-produced hydrogen chloride and excess phosgene are removed under low pressures at a certain point, thereby recovering a part of the isocyanate-containing solution. Therefore, the amine and phosgene are brought into contact in a short period of time in an eddy of a high Reynolds' number and the amine can be converted immediately into its corresponding isocyanate. Reasonable results have been achieved by this method, since organic isocyanates can be continuously produced with a relatively high yield when the concentrations of their corresponding amines are kept relatively low, i.e., in the range of 5–10%. However, more amine is reacted undesirably with the isocyanate, besides the reaction between the amine and phosgene, as the concentration of the amine in the reaction mixture becomes higher, resulting in the formation of byproducts, non-volatile tar-like substances and leading to a lowered yield. Thus, the above method is accompanied by a drawback in that it does not permit the use of amines in a high concentration.

According to Japanese Patent Publication No. 17381/1965, an amine is catalytically reacted with excess phosgene to form a corresponding isocyanate and an intermediate. Before the prestage reaction (100°–110° C.) has been completed, in other words, after a lapse of several seconds to 30 minutes, the reaction mixture is transferred into another reaction system which is maintained at 150°–170° C., where the amine is brought into contact with a mixture of phosgene and hydrochloric acid while maintaining the concentration of hydrochloric acid in the mixture higher than that in a reaction mixture formed through the complete reaction between the phosgene and amine introduced into the first reaction system. The above publication discloses specifically that it is of particular importance for improving the yield of each isocyanate to control the residence time of the reaction mixture in the first reaction system and to adjust the ratio of phosgene to hydrochloric acid within a predetermined range in the second reaction system. The above method has not yet been found to be a fully satisfactory one because it is too complicated to apply it on an industrial scale and it does not permit the use of reactants in high concentrations.

According to Japanese Patent Publication No. 6126/1976, phosgene and an amine are reacted at a temperature of 40°–120° C. and a gauge pressure of 10–50 Kg/cm$^2$ and the carbamyl chloride in the thus-formed reaction mixture is then heated at a temperature of 120°–180° C. and a gauge pressure of 15 Kg/cm$^2$ to continuously prepare an organic isocyanate. In one embodiment of the process disclosed therein, the reaction between phosgene and an amine is carried out while recirculating a reaction mixture through a tubular line which includes at least one gas-liquid separater. The subsequent heating step of the resultant carbamyl chloride is conducted under pressure in a distillation column. In the distillation column, the decomposition of carbamyl chloride into an isocyanate and the evaporation of hydrochloric acid and phosgene take place. A dilute isocyanate mixture, which contains phosgene and drawn out of the distillation column from a bottom part thereof, is subjected to distillation under atmospheric pressure or a slightly raised pressure, thereby isolating an isocyanate-containing solution. As has been known conventionally, the solubility of phosgene in the reaction mixture can be increased to a substantial extent if the reaction is carried out under high pressures such as 10–50 atoms. Such an increased solubility of phosgene serves to accelerate the velocity of the preparation reaction of carbamyl chloride and allows an isocyanate with a good yield to be obtained even if the reactants are present in high concentrations. If the decomposition into carbamyl chloride in the second step is carried out at a high pressure, the condensation of unreacted phosgene can be carried out easily, thereby bringing about an effect that the problem of separating hydrochloric acid can be made easier. However, it is very dangerous from an industrial viewpoint to handle a reaction liquid containing excess phosgene under high pressures. Special consideration must be taken from the viewpoint of safety.

Carbamyl chloride has a low solubility to solvents. When slurry of such a high concentration is recirculated through a tubular line under high pressures, the degree of its corrosiveness to metallic materials increases considerably and commonly-employed stainless steel cannot be used, leading to a substantial increase in the cost of plant and equipment, for example, due to requirement for expensive materials.

Furthermore, the use of the reactants in high concentrations increases not only tar-like by-product substances but also increases the viscosity of the carbamyl chloride slurry to a considerable extent, resulting in the occurrence of tubular line cologging and making the recirculation of the reaction liquid difficult. On the other hand, where a high pressure is employed only in a single stage as in the method disclosed in Japanese Patent Publication No. 6126/1976, sufficiently long residence time is required to complete the reaction in the first sstep because, unless the conversion of the amine hydrochloride formed in the course of the reaction into carbamyl chloride is completed, the decomposition reaction of carbamyl chloride as a second step in a distillation column is impeded by the clogging of the column due to the remaining amine hydrochloride and the yield of the isocyanate is lowered.

SUMMARY OF THE INVENTION

An object of this invention is to provide a process which can continuously prepare an isocyanate with a high yield from its corresponding amine and phosgene.

Another object of this invention is to provide a continuous preparation process for an isocyanate from its corresponding amine and phosgene while suppressing the formation of by-products.

A further object of this invention is to provide a continuous preparation process for an isocyanate from its corresponding amine and phosgene, which process can be carried out safely while enjoying good operability even when the reactants are used in high concentrations.

The present invention thus provides the following continuous preparation process for an organic isocyanate.

In a process of continuously preparing an organic isocyanate by reacting a corresponding organic primary amine and stoichiometrically excess phosgene in an inert organic solvent, the improvement which comprises the steps of:

(a) bringing the organic primary amine in a substantially dispersed state into contact with phosgene at a gauge pressure of 10 Kg/cm$^2$ or lower and a temperature in the range of 60°–100° C., thereby forming a corresponding organic carbamyl chloride, converting the by-produced hydrochloric acid salt of said amine and phosgene into the organic carbamyl chloride, and decomposing 30–70% of the thus-formed organic carbamyl chloride present in the reaction mixture into the organic isocyanate; and (b) maintaining the resultant reaction mixture at a gauge pressure of 10 Kg/cm$^2$ or lower and a temperature in the range of 120°–160° C., thereby converting the hydrochloric acid salt of said amine and phosgene present in the reaction mixture into the organic carbamyl chloride and completing the decomposition of said organic carbamyl chloride into said organic isocyanate.

In the above process, the first step, i.e., Step (a) may be carried out in either a tubular recirculating line or a tank-shaped reaction vessel.

BRIEF DESCRIPTION OF THE DRAWINGS

In the accompanying drawings.

DETAILED DESCRIPTION OF THE INVENTION

Figure 1:
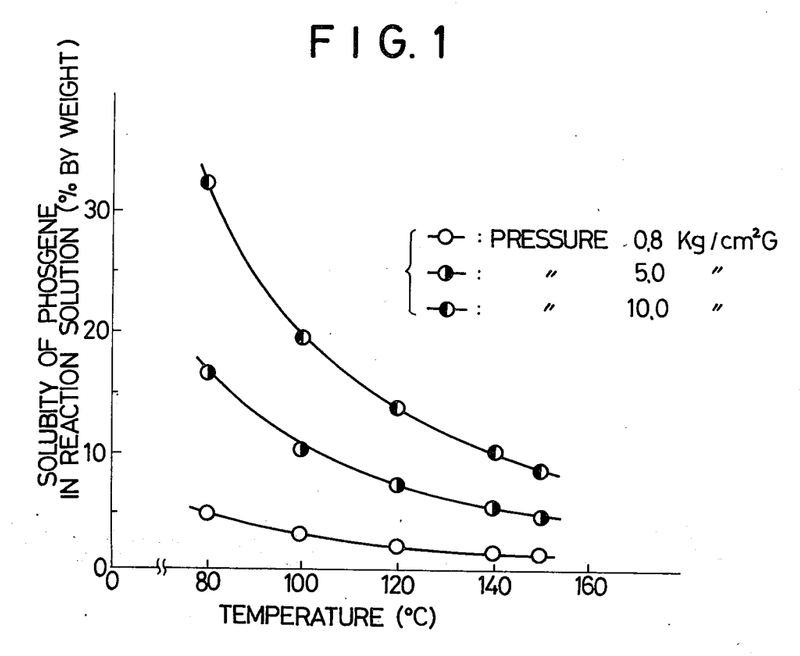
FIG. 1 is a diagrammatic illustration of the relationship at varied pressures between the temperature and the solubility of phosgene in a reaction liquid phase [a 20 wt.% solution of TDI (TDI plus carbamyl chloride as TDI) in o-dichlorobenzene solvent]
Figure 2:
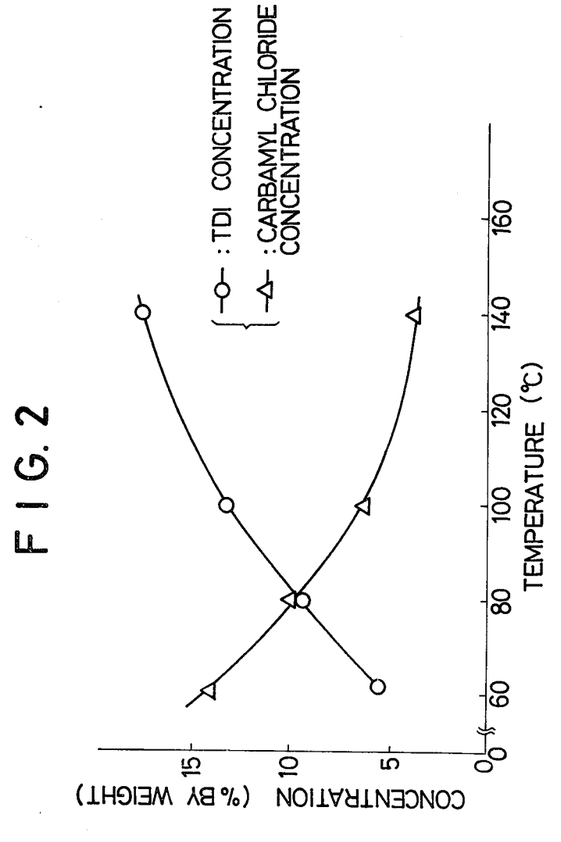
FIG. 2 depicts diagrammatically variations in the equilibrium concentration of each of TDI and carbamyl chloride in a reaction liquid at varied temperatures, when the reaction liquid contains 20 wt.% of TDI (TDI plus carbamyl chloride as TDI) and is maintained at a gauge pressure of 5 Kg/cm$^2$.

As apparent from FIG. 1, the solubility of phosgene is increased substantially by a slight degree of pressurization in the order of a gauge pressure of 5 Kg/cm$^2$ when the temperature ranges from 60° to 100° C. It will also be seen from FIG. 2 that the decomposition equilibrium of carbamyl chloride into TDI can be maintained within a range of 30–70% by maintaining the reaction temperature within a range of 60°–100° C. Thus, different from conducting the reaction at a low temperature below 50° C. under pressurized conditions, it is quite unlikely that the viscosity of the reaction liquid will become considerably high due to the presence of carbamyl chloride in a high concentration and it is quite likely that the amine cannot be dispersed efficiently any longer in a reaction tank. It is also feasible to suppress the formation of byproducts due to the adoption of pressurized conditions even in a highly concentrated reaction liquid by maintaining the reaction temperature below 100° C. and thus holding the decomposition rate of carbamyl chloride at 30% or higher. It has also been found from experimental results that the effect of the pressure on the proportions of carbamyl chloride and isocyanate in a reaction liquid of the first stage reaction is not as great as that of the temperature when the pressure is below 10 Kg/cm$^2$. In addition, it has been discovered that a suitable pressure may be selected from gauge pressures below 10 Kg/cm$^2$ depending on the concentration of the amine to be supplied, the amount of reaction liquid recirculating through the recirculating line, the dispersion speed of the amine, the residence time of the reaction liquid in the reaction system, etc.

The present invention has been completed on the basis of an accumulation of such fundamental data. According to this invention, the concentrations of carbamyl chloride and isocyanate are controlled by suitably selecting the temperature and pressure in the aforementioned first step and the concentration of isocyanate in a reaction liquid may be maintained at about half the level of that in an isocyanate-containing solution to be drawn out in the second step. Accordingly, the chance of reaction between the isocyanate and the starting amine becomes lower, thereby suppressing the formation of byproducts and allowing the isocyanate with a high yield to be obtained even when reactants are present in high concentrations.

The organic primary amine usable in the process according to this invention may be selected from a wide range of unlimited organic primary amines. Exemplary organic primary amines include: aromatic amines such as aniline, toluidine, 2,4-tolylenediamine, 2,6-tolylenediamine, 4,4'-diaminodiphenylmethane, diphenylether diamine, chloroaniline, 3,4-dichloroaniline, tris-(aminoaryl)thiophosphates and tris(aminoaryl)phosphates; aliphatic monoamines such as propyl amine, butyl amine and hexyl amine; and aliphatic diamines such as hexamethylenediamine.

However, the process of this invention is particularly suitable to prepare TDI or MDI from tolylenediamine (hereinafter called "TDA") or diaminodiphenylmethane (hereinafter called "MDA") and phosgene.

The inert organic solvent to be used in this invention may vary extensively. Specific examples of the organic solvent include toluene, benzene, monochlorobenzene and o-dichlorobenzene. Notably, o-dichlorobenzene is preferred.

In the first step, phosgene may be used preferably in an amount at least 50% in excess of required stoichiometrically for a starting amine, in other words, at least 1.5 moles per each NH$_2$ group of every mole of the starting amine, and notably 70–150% in excess.

The first step of the process according to this invention may be practised, as mentioned above, in either a recirculating line or a tank-shaped reaction vessel. Two embodiments of the invention, which are carried out respectively in such a recirculating line and reaction vessel as mentioned above, will hereinafter be described.

First of all, a process, which makes use of a recirculating line, is to be described taking as an example a case of producing TDI or MDI from TDA or MDA while using o-dichlorobenzene as a solvent.

In this process, the molar ratio of phosgene to the amine in an amine-dispersion section of the first step is preferably set, as described above, in such a way that phosgene is present in a chemical equivalent at least 50% excessive, namely, in an amount of at least 1.5 moles per each NH2 group of every mole of the amine, and particularly 70% in excess. The pressure in the closed loop (recirculating line) is below 10 atoms, or preferably 3-7 atoms. This pressure can be obtained by pressurizing and recirculating a slurry containing phosgene and a carbamyl chloride and recirculated through the loop, using a pump. The above pressure can generally be adjusted readily at an exhaust port for the by-produced, hydrochloric acid (off-gas), which is present together with the solvent and phosgene. Since the process is carried out at a low temperature and an elevated pressure, most of the phosgene is recirculated and the actual molar ratio of phosgene to the chemical equivalent of the amine becomes practically a value considerably greater than the above-described molar ratio.

The main feature of the above process resides in that it can be carried out without adversely affecting the yield of the isocyanate even when the concentration of each reactant in the amine-dispersing section of the first step is much higher than that employed in conventional processes. For example, the concentration of the amine may be increased up to 50% by weight. On the other hand, the concentration of the isocyanate at the end of the reaction may be increased up to 30% by weight. In view of the yield of the isocyanate, it is generally preferred to carry out the process by controlling the concentration of the amine within 10-30 wt.% and that of isocyanate at the end of the reaction within 10-25 wt.%.

The reaction temperature in the amine-dispersing section may range from 60° to 100° C. It is rather lower than the optimum reaction temperatures in conventional processes. The reaction liquid is obtained in a slurry form containing the carbamyl chloride and isocyanate. A reaction temperature of 70°-90° C. is particularly preferred when TDA or MDA is used. The reaction pressure is below a gauge pressure of 10 Kg/cm$^2$, and preferably a gauge pressure of 3-7 Kg/cm$^2$. When the concentration of reactants increases beyond 15% by weight, the yield can be sharply improved by pressurizing phosgene. A satisfactory yield is available when phosgene is pressurized to 5 atoms or so. The yield remains at almost the same level even if phosgene is pressurized to 10 atoms or higher. Such a high pressure is rather undesirable from the standpoint of safety when handling excess phosgene.

The reaction in the second step may be carried out by stirring the reactants in a tank-shaped reaction vessel or by recirculating the reactants into a tank-shaped reaction vessel and causing agitation therein. The need for stirring is not so high as in the first step. It is sufficient to recirculate the reaction liquid by a pump only. The reaction temperature in the second step ranges from 120° to 160° C. while the pressure is a gauge pressure of 10 Kg/cm$^2$ or lower. The pressure does not affect the yield of the isocyanate as much as that of the first step.

Taking into consideration the fact that the off-gases of the first and second steps are combined together and excess phosgene is recovered and recirculated, the pressure in the second step may be at the same level as the pressure in the first step or may be somewhat lower than the latter pressure. The pressure of the second step may be built up by charging fresh phosgene or it may be sufficiently reached by introducing phosgene dissolved in the reaction liquid into the second step from the first step.

The residence time in each of the first and second reaction systems according to this invention depends considerably on the temperature employed therein. A residence time of 30-120 minutes is sufficient in the first step for a temperature range of 60°-100° C. It is unnecessary to complete the reaction in the first step. As the residence time of the second step reaction,, there is required a sufficient time period to ensure the complete conversion of the byproduct formed in the first step, i.e., the amine hydrochloride into its corresponding isocyanate. The second step reaction is generally carried out at a temperature in the range of 120°-160° C. for about 10-120 minutes. Here, fresh phosgene may be introduced if necessary.

According to the above-mentioned process, it is possible to considerably increase the molar ratio of phosgene to the chemical equivalent of the amine owing to the increased solubility of phosgene and the recirculation of the reaction liquid and the chance of reaction between phosgene and the amine can thus be increased, by conducting the first step reaction in a tubular recirculating line at a temperature and pressure defined specifically in the above. Since it is also feasible to minimize the chance of reaction between the amine and isocyanate by subjecting 30-70% of the resulting carbamyl chloride to decomposition and maintaining the concentration of the isocyanate below its actual concentration after the completion of the reaction, the isocyanate can be obtained with a high yield and the carbamyl chloride can be kept in a relatively low concentration in the reaction liquid, thereby maintaining the viscosity of the reaction liquid low and permitting easy and efficient recirculation of the reaction liquid through the recirculating line.

Next, the second embodiment, which makes use of a tank-shaped reaction vessel, is to be described taking as an example a case of preparing TDI or MDI from TDA or MDA while using o-dichlorobenzene.

In the present embodiment, the molar ratio of phosgene supplied into the tank-shaped reaction vessel in the first step to the amine is required to be such that phosgene is present in a chemical equivalent at least 50% in excess, namely, in an amount of at least 1.5 moles per each NH2 group of every mole of the amine, and more preferably, 70%-300% in excess. The pressure in the reaction vessel is below 10 Kg/cm$^2$G or, preferably, 3-7 Kg/cm$^2$G. This reaction pressure may be readily adjusted at an exhaust port for the by-product, hydrogen chloride (off-gas), which is generally present together with the solvent and phosgene. Since the first step reaction is carried out at a relatively low temperature and at an elevated pressure, most of phosgene is recirculated and the actual molar ratio of phosgene to the chemical equivalent of the amine becomes substantially greater than the abovedescribed molar ratio.

The main feature of the second embodiment is that the reaction may be effected without deleteriously affecting the yield of the isocyanate even when the concentration of the amine is considerably high in the first step. For example, the amine concentration may be increased up to 50 wt.%. It is feasible to increase the concentration of the isocyanate up to 30 wt.% at the end of the reaction. In view of the yield of the isocyanate, it is normally preferred to control the concentration of the amine within 10-30% by weight or preferably 10-25% by weight and the concentration of the isocyanate at the end of the reaction within 10-25% by weight.

In the reaction vessel, the reaction temperature ranges from 60° to 100° C. The reaction liquid is obtained in a slurry form, which contains the carbamyl chloride and isocyanate. Where TDA or MDA is used, a reaction temperature of 70°-90° C. is especially preferred. As a reaction pressure, a gauge pressure of 10 kg/cm² or lower, or preferably 3-7 kg/cm² is employed. When the concentration of reactants increases beyond 15% by weight, the yield can be sharply improved by pressurizing phosgene. A satisfactory yield is available when phosgene is pressurized to 5 atoms or so. The yield remains almost at the same level even if phosgene is pressurized to 10 atoms or higher. Such a high pressure is rather undesirable from the standpoint of safety when handling excess phosgene.

In the process according to the second embodiment of this invention, the phosgenation reaction of the first step is conducted under the above reaction conditions in a pressure-resistant reaction vessel equipped with a stirrer and heating jacket. Here, the dispersion speed of the amine-containing solution fed through the amine-dispersing tube is maintained at 10-30 m/sec. If the amine-dispersing speed is lower than the lower limit, more by-products, i.e., tar-like nonvolatile residue, will occur even if the reaction temperature is controlled in any way. However, it is not necessary to make the dispersing speed of the amine faster than 30 m/sec by employing a special dispersing tube or applying a special design to the interior of the reaction vessel. Even if the dispersing speed is made faster than 30 m/sec, no change occurs with respect to the amount of by-products. Thus, it is sufficient to maintain the dispersing speed of the amine at 10 m/sec or faster. A suitable dispersing speed of the amine may be selected in accordance with designed reaction factors such as the feed amount of the amine-containing solution, the diameter of the dispersing tube, and the residence time of the reaction liquid. When TDA or MDA is used, the amine may be supplied and dispersed preferably at a flow rate of 20 m/sec or so into a reaction vessel, in which the reaction liquid is agitated at a suitable speed determined in view of the capacity of the reaction vessel and its design, for example, at 350 rpm or so.

In the process according to the second embodiment of this invention, the reaction of the second step may be effected by stirring the reactants in a reaction vessel or by circulating the reactants into a reaction vessel and causing agitation therein. The need for agitation is not so critical as in the first step. It is sufficient to recirculate the reaction liquid by a pump only. The reaction temperature in the second step ranges from 120° to 160° C. while the pressure is a guage pressure of 10 Kg/cm² or lower. The pressure does not affect the yield of the isocyanate as much as that of the first step.

Taking into consideration the fact that the off-gases of the first and second steps are combined together and excess phosgene is recovered and recirculated, the pressure in the second step may be at the same level as the pressure in the first step or may be somewhat lower than the latter pressure. The pressure of the second step may be built up by charging fresh phosgene or it may be sufficiently maintained by introducing the phosgene dissolved in the reaction liquid into the second step from the first step.

Although the phosgenation of unreacted amine hydrocahloride and the decomposition of the carbamyl chloride take place in the second step, the main reaction of the second step is the decomposition reaction of the carbamyl chloride in which decomposition reaction hydrogen chloride is generated. In the process according to the second embodiment of this invention, it is preferred to employ a stirring method which makes use of the hydrogen chloride gas thus generated, in other words, to provide a recirculating line comprising at least one heater and at least one gas-liquid separator and to cause the reaction liquid to recirculate by itself. The reaction liquid may be stirred by its own recirculation without need for any separate power source such as a pump when the reaction liquid accompanied by hydrogen chloride gas generated through the decomposition of carbamyl chloride and phosgene liberated due to a temperature difference ascends through the heater and is allowed to recirculate by itself between the heater and the gas-liquid separator.

In the second embodiment, the residence time in each of the first and second steps is dependent to a considerable extent on the temperature therein. In the first step, a residence time of 30-120 minutes is sufficient for a temperature range of 60°-100° C. It is unnecessary to bring the reaction to completion in the first step. The second step requires sufficient residence time to completely convert the intermediate, i.e., the amine hydrochloride formed in the first step, into the isocyanate. The second step is generally carried out at a temperature in the range of 120°-160° C. for about 10-120 minutes. If necessary, fresh phosgene may be charged in the second step.

According to the above-described second embodiment, the formation of byproducts can be suppressed and the isocyanate can be obtained with a high yield by using a tank-shaped reaction vessel, making the dispersing speed of the starting amine charged into the reaction vessel faster and controlling the amounts of the organic carbamyl chloride and organic isocyanate to be produced, similar to the above-described process which incorporates a tubular loop. In addition, the process according to the second embodiment of this invention can obviate the drawbacks that the above-mentioned process using a tubular loop is accompanied by, namely, that materials making up the tubular loop are subjected to corrosion and a sizable power cost is required for the recirculation of the reaction liquid.

In the aforementioned two processes, the reaction systems for their second steps may be interchanged. In other words, the present invention may be put into practice by combining the first reaction system of the process according to the first embodiment and the second reaction system of the process according to the second embodiment. Alternatively, it is also feasible for the practice of this invention to combine the first reaction system of the process according to the second embodiment and the second reaction system of the process according to the first embodiment.

Various embodiments of this invention are further illustrated in the following example, in which all designations of percent refer to percent by weight unless specified otherwise.

EXAMPLE 1

Figure 3:
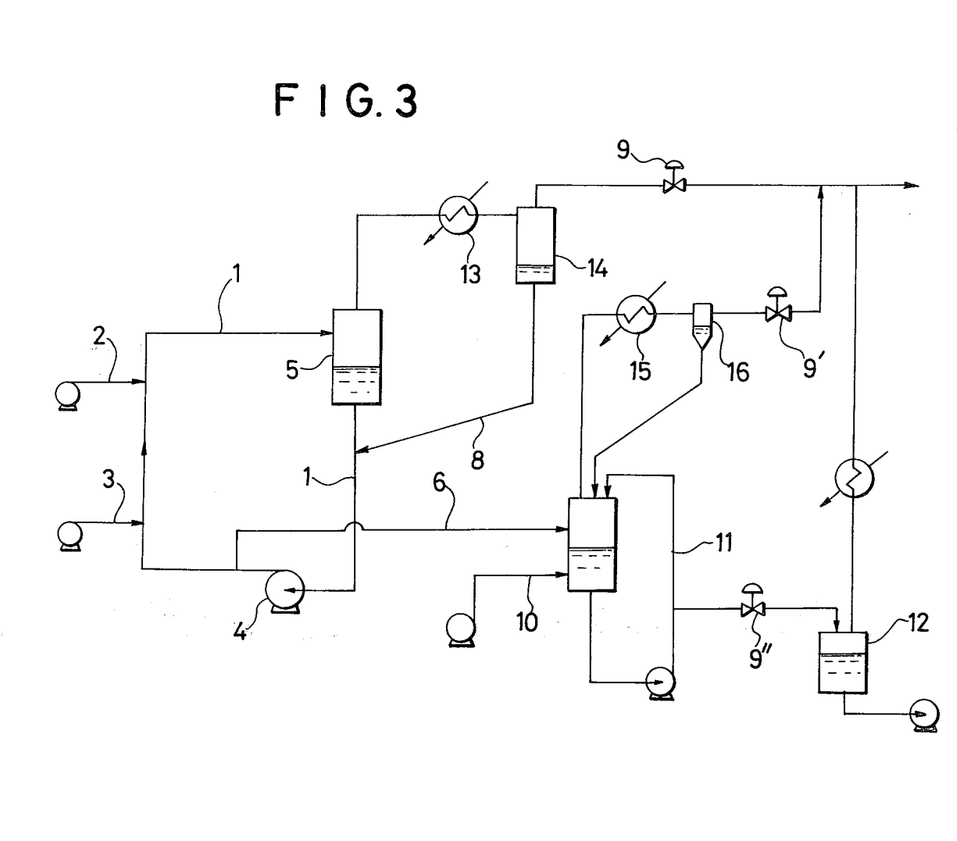
FIG. 3 is a flow sheet showing one embodiment of this invention, which makes use of a tubular recirculating line.

Reference is made to FIG. 3. A tubular recirculating line, which corresponds to the first reaction system, is formed of a reaction tube 1 including an amine-feeding and dispersing tube 2, a phosgene-feeding tube 3 and a fresh solvent-feeding tube (not illustrated), a gas separator 5, and a pump 4 for recirculating the reaction mixture under an elevated pressure through the recirculating line. The second reaction system, in which the decomposition of the carbamyl chloride and the phosgenation of the amine hydrochloride takes place concurrently, is formed of a tank-shaped reaction vessel 7 and a tubular line 11 which is similar to the first reaction system and is adapted to stir a reaction mixture in the reaction vessel 7. At the upper part of the gas separator 5, an off-gas line is connected through a condenser 13 and a condensate reservoir 14 so as to cool the gas exhausted therefrom and return the resultant condensate back into the recirculating line and to exhaust continuously through a pressure-regulating valve 9 an off-gas which is consisted principally of HCl. Similarly, at the upper part of the reaction vessel 7 of the second reaction system through which part the reaction effluent from the first reaction system is continuously charged through the recirculating line into the second reaction system, there is provided an off-gas line having a condenser 15, a condensate reservoir 16 and a pressure-regulating valve 9'.

The tubular recirculating line 1 of the first reaction system shown in FIG. 3 is made of a reaction tube which is in turn made of stainless steel and has an inner diameter of 1 inch. A dichlorobenzene solution containing phosgene and a mixture of TDA isomers was continuously introduced into the line 1. In the recirculating line of the first reaction system, phosgene was charged through the tube 3 at a flow rate of 24.3 Kg/hour (0.246 mole per hour) while being heated by a pressure pump for liquid phosgene. At the same time, an o-dichlorobenzene solution in which the concentration of TDA had been adjusted to 17% was supplied and dispersed into the recirculating line through the tube 2 at a flow rate of 44 Kg/hour (0.061 mole in terms of amine per hour) by means of a pressure pump. The pressure in the first reaction system was maintained at 5.0 Kg/cm²G by the pressure-regulating valve 9 on the off-gas line. In the meantime, an o-dichlorobenzene suspension containing about 5% of the carbamyl chloride and about 5% of TDI as well as excess phosgene was recirculated at a flow rate of 8,200 Kg/hour through the line, which was maintained at 80° C.

As soon as the amine solution was introduced from the dispersing port into the line, it was immediately dispersed in and mixed with the o-dichlorobenzene suspension to undergo a reaction with phosgene. The resultant reaction mixture was then introduced into the gas-liquid separator 5 (capacity: 150 liters) maintained at 80° C., where the by-produced hydrogen chloride was exhausted from the separator and the accompanying solvent and phosgene were condensed by the condenser 13 and returned through the condensate reservoir 14 and a line 8 back into the recirculating loop of the reaction system.

A part of the reaction liquid was continuously fed to the reaction vessel 7 of the second reaction system via a communication line 6. The remaining reaction liquid was recirculated by a pump to the line of the first reaction system, where fresh o-dichlorobenzene was charged at a flow rate of 59.8 Kg/hour so as to maintain the reaction liquid in the recirculating line of the first reaction system at the above-mentioned concentration.

The total hold-up (the amount of reaction liquid retained) in the loop of the first reaction system was about 140 Kg and the residence time was about 1.4 hours. The reaction liquid drawn out of the first reaction system through the line 6 was delivered into the recirculating line of the second reaction system, which recirculating line was kept at 150° C. Phosgene was charged into the reaction vessel 7 (capacity: 130 liters) of the second reaction system at a flow rate of 6 Kg/hour (0.061 mole per hour) via a line 10. The reaction was carried out while maintaining continued stirring in the reaction vessel 7 by recirculating the reaction liquid by a pump through the recirculating line 11 made of a tube whose inner diameter was ¾ inch. During that time, the reaction vessel 7 and the circulating line 11 were maintained at 5.0 Kg/cm²G owing to the provision of the pressure-regulating valve 9' on the off-gas line. Similar to the first reaction system, by-produced hydrogen chloride was removed at the gas-liquid separating part of the reaction vessel 7 of the second reaction system and accompanying solvent and phosgene were then condensed at the condenser 15 and returned to the second reaction system.

The total hold-up of the second reaction system was about 150 Kg and the residence time was about 1.5 hours. A part of the reaction liquid of the second reaction system was drawn out and, subsequent to being reduced in pressure at a pressure-regulating valve 9'', introduced into a flash tank 12 and then subjected to degasfication in a degasification tower. The thus-obtained isocyanate-containing solution was subjected to distillation analysis in accordance with a commonly-known method. The distillation analysis indicated that it contained 10.5% of TDI and 0.5% of non-volatile residue.

COMPARATIVE EXAMPLE 1

The procedure of Example 1 was repeated using the same apparatus as that used in Example 1, except for the adoption of 140° C. and 0.8 Kg/cm²G for the first reaction system and 0.8 Kg/cm²G for the second reaction system. The resultant isocyanate-containing solution contained 9.8% of TDI and 1.1% of non-volative residue. Thus, more residue was contained compared with the experimental result obtained in Example 1.

EXAMPLE 2

Using the same apparatus as that used in Example 1, an experiment was carried out in much the same way as in Example 1 under the following conditions:

| First reaction system | |
|---|---|
| Flow rate of TDA (25% solution in o-dichlorobenzene) | 44 Kg/hour |
| Flow rate of phosgene | 40.1 Kg/hour |
| Flow rate of o-dichlorobenzene | 14.1 Kg/hour |
| Temperature | 80° C. |
| Pressure in recirculating loop | 5.0 Kg/cm²G |

A distillation analysis of the thus-obtained isocyanate-containing solution indicated that it contained 24.8% of TDI and 1.3% of non-volatile residue.

Furthermore, the above procedure was followed except that the supply of phosgene was changed to 49.1 Kg/hour and the pressure in the recirculating loop was increased to 10.0 Kg/cm²G. Upon subjecting the resultant isocyanate-containing solution to distillation analysis, it was found that it contained 24.5% of TDI and 1.2% of non-volatile residue. Thus, the content of the non-volatile residue was almost equal to that in the isocyanate-containing solution obtained by setting the pressue at 5.0 Kg/cm²G in Example 2.

COMPARATIVE EXAMPLE 2

The procedure of Example 2 was repeated using the same apparatus as that used in Example 1 except for the employment of 140° C. and 0.8 Kg/cm$^2$G for the first reaction system and 0.8 Kg/cm$^2$G for the second reaction system. A distillation analysis of the resultant isocyanate-containing solution indicated that it contained 23.0% of TDI and 3.2% of non-volatile residue. Accordingly, the content of non-volatile residue was increased compared with the test results obtained in Example 2.

COMPARATIVE EXAMPLE 3

The procedure of Example 2 was repeated using the same apparatus as that used in Example 1 except that the temperature of the first reaction system was set at 120° C. Upon subjecting the resultant isocyanate-containing solution to distillation analysis, it was found that the isocyanate-containing solution contained 24.0% of TDI and 2.1% of non-volatile residue. Compared with the results obtained in Example 2, more residue was contained.

EXAMPLE 3

Preparation of crude MDI was carried out following the procedure of Example 1 while using the same apparatus as that used in Example 1, except for the substitution of crude MDA containing 15.9% of NH$_s$ as the starting material for TDA.

The resultant reaction liquid was subjected to distillation so as to cause o-dichlorobenzene to evaporate off. A distillation analysis of the resultant bottom indicated that the resultant crude MDI of a light brown color contained 32.5% of NCO and 0.02% of hydrolyzable chlorine and had a viscosity of 40 cps at 25° C.

EXAMPLE 4

Figure 4:
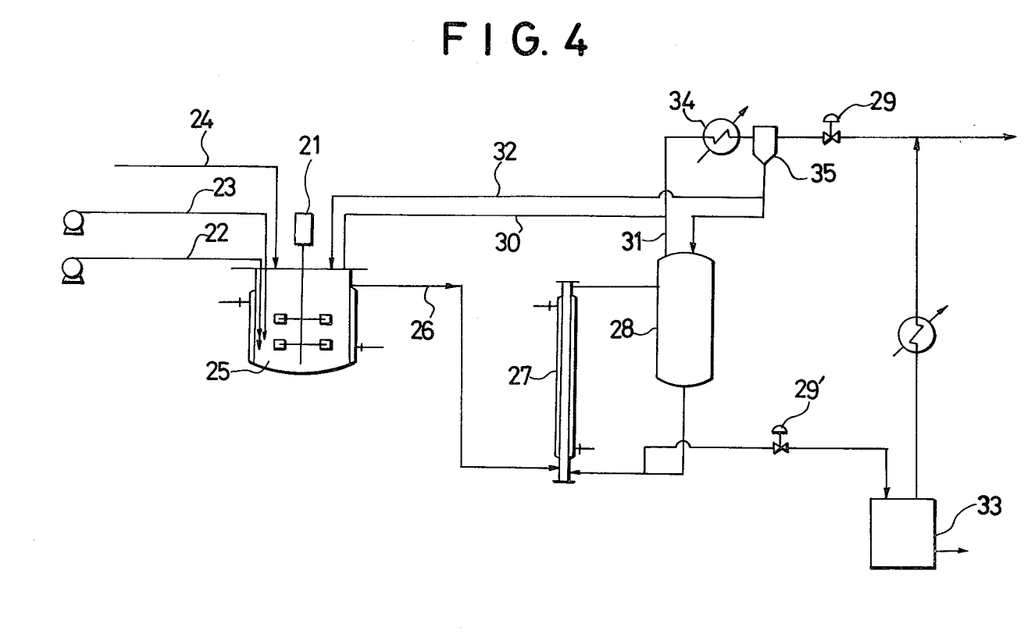
FIG. 4 is a flow sheet illustrating another embodiment of this invention, in which a tank-shaped reaction vessel is used.

Reference is made to FIG. 4, in which the first tank-shaped reaction system is formed of a 50-liter, pressure-resistant reaction vessel 25 equipped with a jacket and having a stirrer 21 provided with stirring propellers, an amine-feeding and dispersing tube 22, a phosgene-feeding tube 23 and a fresh solvent-feeding tube 24.

The second reaction system, in which the decomposition of the carbamyl chloride and the phosgenation of the amine hydrochloride take place simultaneously, is formed of a recirculating loop having an externally-heated tube 27 and a gas-liquid separator 28.

Off-gas lines 30 and 31 of the first and second reaction systems are combined into a single off-gas line. Thus, the gases from the lines 30 and 31 were cooled at a condenser 34 and the resulting condensate was returned through a condensate reservoir 35 to the first and second reaction systems. Uncondensed off-gas, which consisted principally of hydrogen chloride, was continuously exhausted outside the systems through a pressure-regulating valve 29.

The reaction vessel of the first reaction system depicted in FIG. 4 is a pressure-resistant reaction vessel 25 made of stainless steel and having an inner diameter of 350 mm, in which a reaction liquid was continuously stirred at 350 rpm. An o-dichlorobenzene solution containing phosgene and a mixture of TDA isomers was continuously charged into the pressure-resistant reaction vessel 25. Phosgene was supplied through the tube 23 at a flow rate of 40.1 Kg/hour (0.4054 Kmole per hour) through a pressure pump for liquid phosgene. On the other hand, an o-dichlorobenzene solution, in which the concentration of TDA had been adjusted to 25%, was supplied and dispersed at a flow rate of 44 Kg/hour (0.0902 Kmole in terms of amine per hour) by a pressure pump. Here, the jetting out velocity of the TDA solution into the reaction vessel was maintained at 20 m/sec at the outlet of the dispersing tube.

The off-gas lines of the first and second reaction systems were combined into a single off-gas line. Its pressure was kept at 5.0 Kg/cm$^2$G by the pressure-regulating valve. The above amine-containing solution was immediately dispersed and mixed as soon as it was introduced through the dispersing port and the amine underwent a reaction with phosgene. After maintaining the reaction mixture at 80° C. in the reaction vessel, there was obtained an o-dichlorobenzene suspension containing about 10% of TDI and about 10% of the carbamyl chloride.

By-produced hydrogen chloride was exhausted through the line 30 and accompanying solvent and phosgene were condensed at the condenser 34 and then returned to the first reaction system via the condensate reservoir 35 and the line 32.

The hold-up in the reaction vessel of the first reaction system was about 49.5 Kg and the residence time therein was 0.6 hour. A part of the reaction liquid was discharged as a surplus through an overflow tube 26 and fed to the lower part of the externally-heated tube 27 of the reactor of the second reaction system. The second reaction system was a recirculating loop which comprised a heating tube having a capacity of 6 liters and equipped externally with a heating jacket and a tank-shaped gas-liquid separater 28 having a capacity of 100 liters. As soon as the reaction liquid of the first reaction system entered the heating tube 27, hydrogen chloride gas was generated due to the decomposition of the carbamyl chloride and, at the same time, phosgene was evaporated due to a difference in its solubility in the reaction liquid between the first reaction system and the second reaction system. Accordingly, a flow of these gases occurred toward the upper part of the heating tube 27, whereby causing the reaction liquid to recirculate by itself in the second reaction system. In the meantime, the gas, which had generated in the phosgenation reaction, was separated at the gas-liquid separator 28 and exhausted as an off-gas through the line 31.

The hold-up in the second reaction system was about 81 Kg and its residence time was 1 hour. A part of the reaction liquid was drawn out of the second reaction system due to a pressure difference and, after being reduced in pressure through the pressure-regulating valve 29', was introduced into a flash tank 33 and then degasified at a degasification column. A distillation analysis of the thus-obtained isocyanate-containing solution by an ordinary method indicated that it contained 19.8% of TDI and 1.1% of non-volatile residue.

COMPARATIVE EXAMPLE 4

The procedure of Example 4 was repeated using the same apparatus as that used in Example 4 except that, in the first reaction system, the feed TDA solution was blown into the reaction vessel at 7 m/sec. The thus-obtained isocyanate-containing solution was found, through its distillation analysis, to contain 19.2% of TDI and 1.7% of non-volatile residue.

COMPARATIVE EXAMPLE 5

The procedure of Example 4 was followed using the same apparatus as that used in Example 4 except that the temperature, pressure and blowing speed of the feed TDA solution into the reaction vessel in the reaction system were set respectively at 140° C., 0.8 Kg/cm$^2$G and 20 m/sec and the pressure in the second reaction system was set at 0.8 Kg/cm$^2$G. Upon subjecting the thus-obtained isocyanate-containing solution to distillation analysis, it was found that it contained 19.0% of TDI and 2.0% of non-volatile residue.

EXAMPLE 5

Crude MDI was prepared by following the procedure of Example 4 in the same apparatus as that used in Example 4 except for the substitution of crude MDA containing 15.9% of NH$_2$ group as a starting material for TDA.

The reaction liquid was subjected to distillation, thereby causing o-dichlorobenzene to evaporate off. An analysis of its bottom indicated that the resultant crude MDI contained 32.4% of NCO and 0.02% of hydrolyzable chlorine and had a viscosity of 40 cps at 25° C.

What is claimed is:

1. In a process for continuously preparing an organic isocyanate by reacting a corresponding organic primary amine and stoichiometrically excess phosgene in an inert organic solvent, the improvement which comprises the steps of:
   (a) bringing the organic primary amine in a practically dispersed state into contact with phosgene at a gauge pressure of 2–7 Kg/cm$^2$ and a temperature in the range of 60°–100° C., thereby forming a corresponding organic carbamyl chloride, converting the bi-produced hydrochloric acid salt of said amine, and phosgene into the organic carbamyl chloride and decomposing 30–70% of the thus-formed organic carbamyl chloride present in the reaction mixture into the organic isocyanate; and
   (b) maintaining the resultant reaction mixture at a gauge pressure of 3–7 Kg/cm$^2$ and a temperature in the range of 120°–160° C., thereby converting the hydrochloric acid salt of said amine and phosgene present in the reaction mixture into the organic carbamyl chloride and completing the decomposition of said organic carbamyl chloride into said organic isocyanate.

2. The process according to claim 1, wherein said organic primary amine is practically dispersed by supplying through dispersing means said organic primary amine into phosgene in an amount of at least 1.5 moles per each amino group of every mole of said amine, which phosgene is recirculated together with the inert organic solvent through a tubular recirculating line.

3. The process according to claim 1, wherein said organic primary amine is practically dispersed by supplying through dispersing means said organic primary amine at a flow rate of 10–30 m/sec into phosgene in an amount of at least 1.5 moles per each amino group of every mole of said amine, which phosgene is present together with the inert organic solvent in a tank-shaped reaction vessel.

4. The process according to claim 1, wherein the reaction under pressure in step (b) is carried out in a recirculating line which includes a heating tube and a gas-liquid separator.

5. The process according to claim 1, wherein said organic primary amine is selected from tolylene diamine and diaminodiphenylmethane.

6. The process according to claim 5, wherein phosgene is supplied in step (a) in an amount of 3.4–8 moles per mole of the amine.

7. The process according to claim 5, wherein the inert organic solvent is o-dichlorobenzene.

8. The process according to claim 1, wherein the residence time of the reaction mixture in step (a) is 30–120 minutes.

9. The process according to claim 1, wherein the residence time of the reaction mixture in step (b) is 10–120 minutes.

10. The process according to claim 1, wherein the concentration of the organic primary amine in step (a) is 10–30% by weight in a dispersion zone of said amine.

11. The process according to claim 1, wherein the concentration of the organic isocyanate at the end of the reaction in step (a) is 10–25% by weight.

12. The process according to claim 5, wherein the reaction temperature in step (a) is 70°–90° C.

* * * * *